United States Patent
Fan

(10) Patent No.: US 9,820,736 B1
(45) Date of Patent: Nov. 21, 2017

(54) LAPAROSCOPIC SUTURE LOOP MAKER

(71) Applicant: Peter Fan, Englewood Cliffs, NJ (US)

(72) Inventor: Peter Fan, Englewood Cliffs, NJ (US)

( * ) Notice: Subject to any disclaimer, the term of this patent is extended or adjusted under 35 U.S.C. 154(b) by 0 days.

(21) Appl. No.: 15/390,801

(22) Filed: Dec. 27, 2016

(51) Int. Cl.
*A61B 17/04* (2006.01)

(52) U.S. Cl.
CPC .. *A61B 17/0469* (2013.01); *A61B 2017/0474* (2013.01); *A61B 2017/0475* (2013.01)

(58) Field of Classification Search
CPC ........ A61B 17/0469; A61B 2017/0474; A61B 2017/0475
See application file for complete search history.

(56) References Cited

U.S. PATENT DOCUMENTS

| | | | | |
|---|---|---|---|---|
| 4,635,638 A | * | 1/1987 | Weintraub | A61B 17/0469 269/140 |
| 5,938,668 A | * | 8/1999 | Scirica | A61B 17/0469 606/139 |
| 5,954,731 A | * | 9/1999 | Yoon | A61B 17/062 606/139 |
| 6,017,358 A | * | 1/2000 | Yoon | A61B 17/29 600/564 |
| 6,086,601 A | * | 7/2000 | Yoon | A61B 17/062 606/139 |
| 2008/0228204 A1 | * | 9/2008 | Hamilton | A61B 17/0491 606/148 |

* cited by examiner

*Primary Examiner* — Ashley Fishback

(57) ABSTRACT

There are many methods of tying a knot in a surgical suture. One method is to form a loop in the suture and then pull the other end of the suture through the loop. To do this laparoscopically is the object of the present invention. The finger loop handles of two small diameter laparoscopic graspers are sacrificed, and their shafts are then placed within a single common sheath, using also a single common in-line handle. The jaws of the graspers are operated by spring loaded push knobs on the handle. A loop is formed by grasping the same suture at two points a short distance apart simultaneously with the two graspers, and then bringing them together. The present invention is capable of doing this by virtue of one of the two graspers being slide-able, extendable and retractable.

2 Claims, 9 Drawing Sheets

LAPAROSCOPIC SUTURE LOOP MAKER

FIELD OF THE INVENTION

The tying of knots in a suture intra-corporeally with laparoscopic instruments is generally difficult. The present device is a hand operated laparoscopic instrument which helps creating a loop in a suture, thus facilitating the tying process. It may also be adapted for use in open surgery or in deep cavities where the fingers cannot reach, or for use by a robot.

BACKGROUND OF THE INVENTION

Tying of knots is essential in any kind of surgery. It is relatively easy in open surgery, but is difficult in laparoscopic surgery. The current art of laparoscopic knot tying employs either the extra-corporeal method, involving tying the knot by hand outside the body and pushing the knot inside with a knot pusher, or the intra-corporeal method, involving manipulation of the suture with the tips of two laparoscopic graspers, which is slow and cumbersome, and requires considerable skill. Laparoscopic clip appliers, staplers, pre-tied knots and the like are useful substitutes, but cannot totally replace tied knots which are still needed. Despite considerable prior art, today hardly any hand operated instrument exists that renders laparoscopic intra-corporeal knot tying easier and faster.

In order to describe the tying process, the different parts of the suture ligature need first be given names. As shown in FIG. 18 in the drawings, after the suture ligature has passed around the tissue to be tied, it then presents with a head end (1), a tail end (2), a leading strand (3) and a tail strand (4), There are three basic methods of tying a knot, whether done openly or laparoscopically. One method is making a "throw" which involves passing the head end of the suture around its tail strand. This is quite simple as in the tying of shoe laces with fingers. It does however involve a critical step which is the passing or release and re-grab of the head end of the suture, and wrapping it around the tail strand. In laparoscopic surgery this is difficult because the graspers are trapped in the abdominal wall, and the surgeon is limited to using only two laparoscopic graspers, one in each hand.

The second method is making the head end of the suture pass 360 degrees continuously around the tail strand, as is done in the "Automatic Laparoscopic Knot Tying Instrument", invented by this author, and is noted for avoiding the release and re-grab (see application Ser. No. 14/973,858).

The third method involves making a loop or loops, which is the common practice by surgeons performing open surgery, where the surgeon makes "instrument ties", by wrapping the leading strand of the suture once or several times around the needle holder, and then pulls the tail end of the suture through the loop or loops. This is impossible with the laparoscopic grasper because the instrument is trapped in the abdominal wall. There have been many different attempts in the prior art trying to make a loop laparoscopically, but none has been effective. The instrument described here is yet another method of making a loop laparoscopically.

In the present invention two small diameter laparoscopic graspers without their handles are incorporated inside a common shaft, with one being stationary and the other extendable and retractable. Two points along the leading strand of the same suture a short distance apart are grasped simultaneously by the jaws of the two graspers. Bringing these two points together forms a loop, with the loop being formed by the portion of the suture between these two points. The tail end of the suture is then brought through the loop by a second instrument in the operator's other hand, thus forming a knot. The operator however must ensure that the loop thus formed is a closed loop, not an open loop. The closed loop is where the loop faces towards the opposing end of the suture, and not away from it. An open loop results where the loop and the opposing end of the suture both face in the same direction.

Referring to the prior art, the most recent is the author's Automatic Laparoscopic Knot Tying Instrument, which uses a mini-grasper at the tip of the instrument grasping the head end of the suture, capable of rotating through 360 degrees around the tail strand, without releasing and re-grabbing the head end of the suture. Included in the prior art is also the author's previous unsuccessful attempt at making a Double Laparoscopic Grasper which was intended to pass the head end of the suture from one grasper to the other across the tail end of the suture. The Christoudias Double Grasper has 3 jaws, with a common middle jaw, but functions as a tissue approximator. Its spring loaded actuators are operated by two push buttons. The Ferzli Double Grasper, has a second pair of jaws positioned more proximally on the main shaft, whose purpose is to anchor one end of the suture prior to twisting it around the shaft of the instrument in order to produce a loop. The Hasson Suture Tying Forceps, is similar to the Ferzli, with 3 finger loops. The orthopedic suture passers are for passing sutures only through hard tissue, and these include the Arthrex Scorpion Suture Passer, and the Arthrex Birdbeak Suture Passer. Some suture passers are for passing sutures through a thickness of soft tissue such as the abdominal wall, and these include the Goretex and the Aesculap. There are devices which "pass the suture-needle" side to side, for inserting sutures into tissues, as well as for tying knots, e.g. the Autosuture's Endo-stitch, and the Japanese Maniceps. Note these only pass the suture needle, not the suture thread per se. There have been devices that attempt to "automatically" tie a knot, such as Jerrigan's experimental rotating slotted disc designed for robotic endocardiac surgery, but it was abandoned because of the requirement for a manufactured cartridge.

There have been also many devices that help to "create a loop", but with each functioning differently—(a) Kitano's grasper with the rotating sleeve, Japanese, (b) Donald Murphy's grasper with the extra horn, Australian, (c) Grice's sleeve catching instrument, (d) Bagnato & Wilson's device which simulates the radiological pig-tail catheter, with a preformed loop built into the tip of the catheter, which is deformable and purportedly a loop former, but it is difficult to manufacture and apply, and has not yet been reduced to practice, (e) Ferzli's double grasper, which anchors one end of the suture, as described above. There have been devices using a "pre-formed knot", (1) Ethicon's Endo-Loop, (2) the Duraknot, (3) LSI's device, (4) Pare's pre-tied knot, all of which do not help to tie knots.

Past inventions related to intra-corporeal laparoscopic knot tying fail to address the basic problem of "making a loop". They usually offer various alternatives, such as making fishing knots, using pre-tied knots, knot pushers, suture clips, cinchers, tissue fasteners, anchors, stapling devices, etc. The present invention however will assist in the manual making of a loop in the suture, helping with intra-corporeal knot tying.

U.S. PATENT DOCUMENTS

1. U.S. Pat. No. 3,834,395 Sep. 10, 1974 Manuel Santos 128/326

2. U.S. Pat. No. 5,201,759 Apr. 13, 1993 George Ferzli. 606/139
3. U.S. Pat. No. 5,217,471 Jun. 8, 1993 Stephen Burkhart 606/148
4. U.S. Pat. No. 5,234,443 Aug. 10, 1993 Phan & Stoller 606/148
5. U.S. Pat. No. 5,250,054 Oct. 5, 1993 Lehmann Li 606/148
6. U.S. Pat. No. 5,281,236 Jan. 25, 1994 Bagnato et al. 606/139
7. U.S. Pat. No. 5,312,423 May 17, 1994 Rosenbluth & Brenneman 606/148
8. U.S. Pat. No. 5,395,382 Mar. 7, 1995 DiGiovanni et al. 606/148
9. U.S. Pat. No. 5,437,682 Aug. 1, 1995 Drew Grice 606/148
10. U.S. Pat. No. 5,423,836 Jun. 13, 1995 Scott Brown 606/148
11. U.S. Pat. No. 5,439,467 Aug. 8, 1995 Theodore Benderev, et al. 606/139
12. U.S. Pat. No. 5,480,406 Jan. 2, 1996 Nolan et al. 606/139
13. U.S. Pat. No. 5,728,109 Mar. 17, 1998 Schulze et al. 606/148
14. U.S. Pat. No. 5,810,852 Sep. 22, 1998 Greenberg et al. 606/148
15. U.S. Pat. No. 5,814,054 Sep. 29, 1998 Kortenbach et al. 606/139
16. U.S. Pat. No. 5,846,254 Dec. 8, 1998 Schulze et al. 606/228
17. U.S. Pat. No. 6,051,006 Apr. 18, 2000 Shluzas & Sikora 606/148
18. U.S. Pat. No. 6,086,601 Jul. 1, 2000 InBae Yoon 606/148
19. U.S. Pat. No. 6,221,084 Apr. 24, 2001 R. Fleenor, Pare Surgical 606/148
20. U.S. Pat. No. 6,432,118 Aug. 13, 2002 Mollenhauer & Kucklick 606/148
21. U.S. Pat. No. 6,716,224 Apr. 26, 2004 Singhatat 606/148
22. 2009/0228025 Sep. 10, 2009 Steven Benson 606/144
23. 2010/0016883 Jan. 21, 2010 George Christoudias 606/205
23. U.S. Pat. No. 5,312,423 May 17, 1994 Rosenbluth et al. 606/148
25 U.S. Pat. No. 8,512,362 Aug. 20, 2013 Ewers et al. 606/158

OTHER PUBLICATIONS

1. Endo-stitch—Autosuture—Manufacturer's item #173016.
2. Maniceps—Japanese suturing device, similar to Endo-stitch.
3. A Laparoscopic Device for Minimally Invasive Cardiac Surg (rotating slotted disc). Shaphan Jernigan, et. al.—European J. of Cardio-thoracic Surgery, Vol. 37, p. 626-630. March 2010.
4. Knot Tying Intra-corporeally, with newly designed Forceps. (sliding sleeve).
5. Kitano et. al.—J. of Minimal Invasive Therapy & Allied Tech, 1996. 5: 27-28.
6. Endoscopic Knot Tying Made Easier—(one jaw with extra bump).
7. Donald Murphy—ANZ J. Surg. 1995. 65, 507-509.
8. The Excalibur Suturing Needle Holder—(jaw with prominent heel, helps looping)
9. Uchida et. al. Surgical Endoscopy—vol. 3, 531-532
10. Alijizawi laparoscopic auto-knot device—(two dissolving balls).
11. A New Reusable Instrument designed for simple and secure knot tying in laparoscopic surgery. S. S. Miller 1996 Surg. Endos 10: 940-941 (pointed canula).
12. The Nobel Automatic Laparoscopic Knotting and Suturing Device. Mishra et. al. World Laparoscopy Hospital, India. (a knot pusher)
13. Automated Knot Tying for Fixation in Minimally Invasive Robot Assisted Cardiac Surgery. March 9(1):105-12.
14. Kuniholm & Buckner—J. Biomed Eng. November 2005, Vol. 127, 1001-8. JSLS. 2005 Jan. 17.
15. M I Frecke—Laparoscopic multifunctional instruments: design and testing. Endosc Surg Allied Technol. 1994 December; 2(6):318-9.
16. G. Berci—Multifunctional laparoscopic Instruments.
17. http://www.ligasure.com/ligasure/pages.aspx?page=Products/Laparoscopi
18. http://www.freepatentsonline.com/y2010/0063437.
19. http//www.ncbi.nlm.nih.gov/pubmed/15791983 Multifunctional Laparoscopic Instruments.
20. Peter Fan—U.S. patent application Ser. No. 14/973,858, Automatic Laparoscopic Knot Tying Instrument.

SUGGESTED U.S. CLASSIFICATION: 606/139, 144, 145, 148.
SUGGESTED INTERNATIONAL CLASSIFICATION: A61B 17/00, 04, 28.
FIELD OF SEARCH: 606/139, 144, 145, 147, 148, 150, 151, 127, 128, 606/167, 168, 170, 174, 182, 185, 205, 207, 210, 211.
RELATED PRIOR PATENTS: U.S. Pat. No. 9,194,468. Ser. No. 14/973,858.

SUMMARY OF THE INVENTION

In laparoscopic surgery, the tying of knots intra-corporeally is technically difficult and requires considerable skill and practice. The advent of laparoscopic clips and staples has been a great blessing to surgeons, but cannot totally replace the use of tied knots, which is still necessary. The instrument presented here helps laparoscopic knot tying by making a loop in the suture. It conforms to the customary shape and size of a laparoscopic instrument, with an elongated round sheath, an in-line handle at the proximal end, and two small diameter graspers protruding at the distal end. The jaws of the graspers are controlled by spring loaded push knobs on top of the handle. One grasper is stationary and non-mobile, while the other is extendable and retractable, being manipulated by the thumb. Two points along the same suture a short distance apart are simultaneously grasped by the jaws of the two graspers, and then brought together and past each other, forming a loop in the suture. The tail end of the suture is then pulled through the loop with another instrument forming a knot.

BRIEF DESCRIPTION OF THE DRAWINGS

The instrument consists of two main sub-assemblies, an in-line handle sub-assembly seen in FIG. 10, and a main shaft sub-assembly seen in FIG. 16.

DETAILED DESCRIPTION OF THE PREFERRED EMBODIMENT

During final assembly, the tip of the main shaft sub-assembly is inserted into the rear of the hollow handle, then out of its neck, and pulled out completely until the flange of the rear spacer is stopped by the inside wall of the handle. The main shaft is then locked to the neck of the handle by the two hexagonal screws. The end cap is inserted into the rear of the handle.

The long slot on the left side of the upper surface of the straight in-line handle is necessary because of the required long travel of the extendable grasper, and because of the need to free up the thumb for actuation. In the scissors type or the pistol type of handles, the thumb could not be utilized for this purpose.

The short slot on the front right side of the handle exists on the upper surface as well as on the bottom surface of the handle. The knob on the top could be pushed by the thumb, the one on the bottom could be pulled by the index finger. Therefore this mechanism could be either pushed or pulled, in addition to being spring loaded. Pulling will provide extra gripping power to the jaws, in addition to that provided by the spring. To permit this to happen, the stem of this knob is intentionally positioned in the mid-range of the slot when at rest.

The jaws of the graspers, and indeed the entire jaw sub-assembly are commercially available, and are therefore considered to be prior art. However the gripping surfaces of the jaws are intentionally placed in the horizontal plane, so the up and down movements of the jaws will not interfere with each other.

The jaws of the stationary grasper are opened by pushing forwards the knob 3 with the thumb. The jaws of the extendable grasper are similarly opened by pushing forwards with the thumb on knob 5. However pushing forwards knob 5 will also push forwards the entire extendable grasper, which has the same effect as pushing forwards the knob 4, which does not matter. It does mean that the jaws of the extendable grasper are in the open position as the grasper is extended forwards. More importantly, at the end of the forward travel of the extendable grasper, one needs to release the smaller knob 5 from under the thumb, in order for the jaws to close on the suture, whilst maintaining forward pressure on the knob 4 keeping the grasper extended. Retraction of the extendable grasper may subsequently be performed by the thumb pulling it backwards, or automatically by a longer compression spring (not shown here) which could be installed over the rear portion of the sheath of the extendable grasper within the handle.

Figure 1:
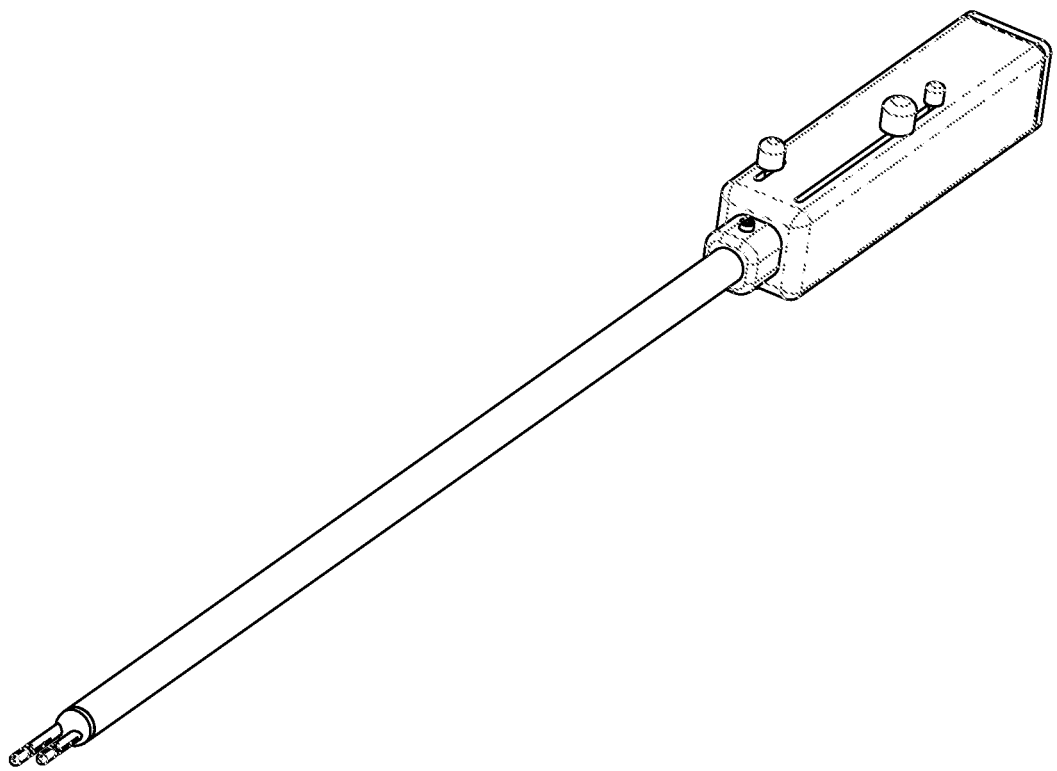
FIG. 1 is perspective view of the entire device from the left side.
Figure 2:
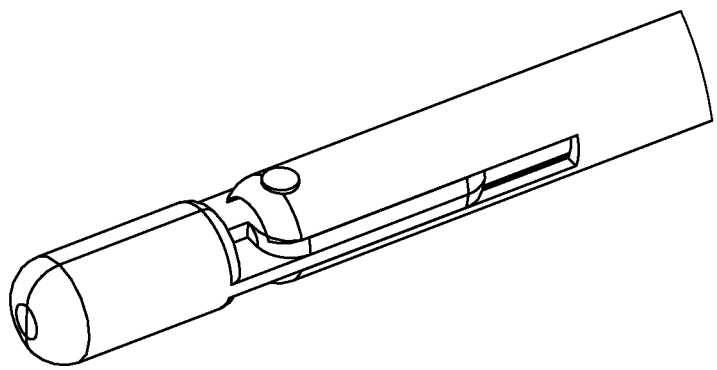
FIG. 2 is a perspective view of the closed jaws at the tip of one of the graspers.
Figure 3:
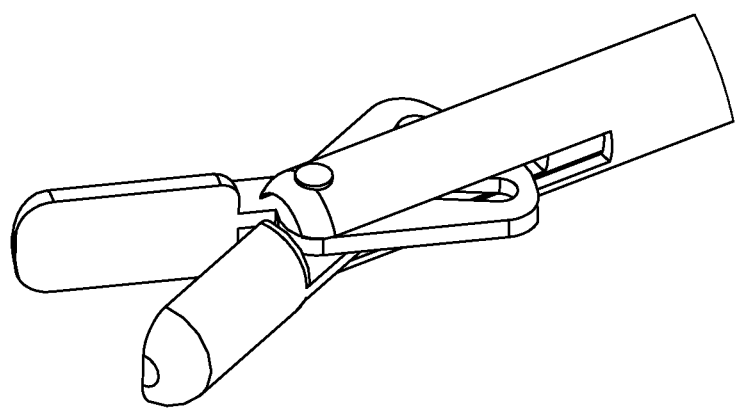
FIG. 3 is perspective view of the jaws in the open position.
Figure 4:
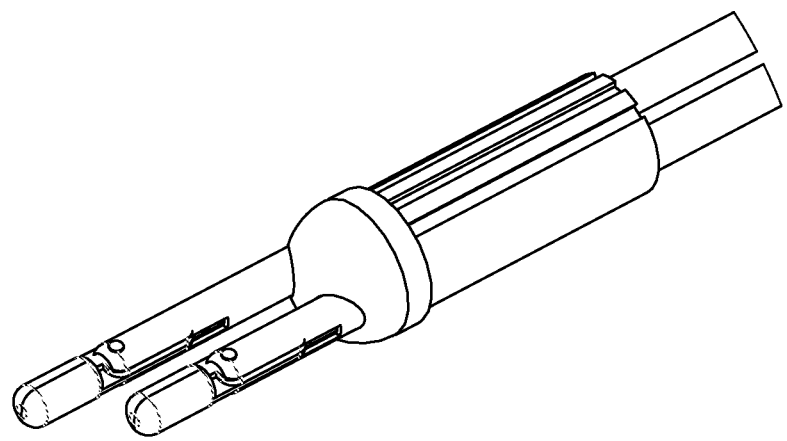
FIG. 4 is a perspective view of the tip of the entire instrument showing the intentional uneven resting position of the tips of the two graspers, with the stationary grasper protruding out more than the extendable grasper.
Figure 5:
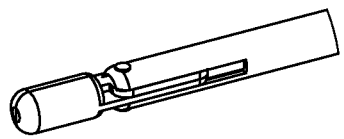
FIG. 5 is a perspective view of a single jaw sub-assembly.
Figure 6:
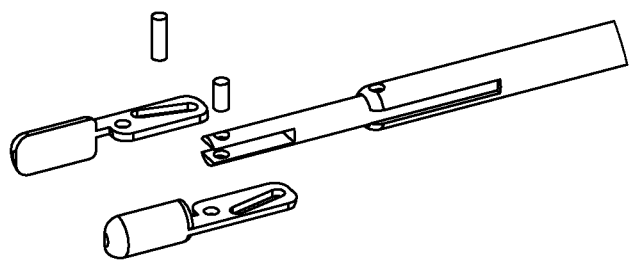
FIG. 6 is an exploded view of the parts of one jaw sub-assembly. Part 14 is a miniature tubular sheath which extends all the way back to the handle. Inside this sheath is a rod 15, also extending all the way back to the handle. Parts 18 and 19 are jaw blades which are inter-connected to the operating rod 15, through the pins 20 and 22, and through the oblique slot 21 in the blades of the two jaws. The jaws will open or close as the rod 15 slide up or down the sheath 14. Numbers 16 and 17 refer to the same parts in the second jaw sub-assembly, not shown here.
Figure 7:
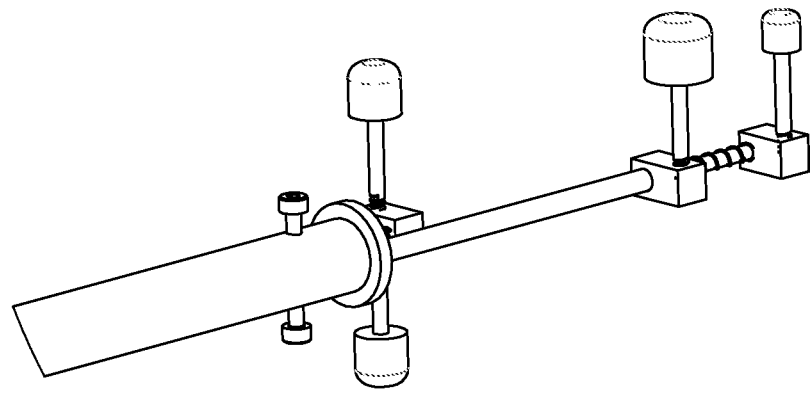
FIG. 7 is a perspective of the sliding mechanism of the extendable grasper on the left side of the device, with a larger knob 4 connected to the grasper's sheath through a larger connector 12. The operating rod of this extendable grasper is similarly connected to a smaller knob 5 through a smaller connector 11. A compression spring 18 holds the rod in a rear direction constantly. Note the grasper on the handle's right side is stationary, and bears a knob 3 on top as well as a knob on the bottom side 6.
Figure 8:
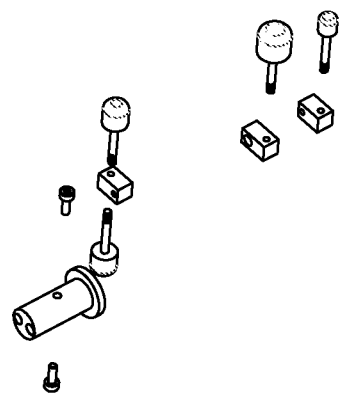
FIG. 8 is an exploded view of the three connectors, the four knobs, the rear spacer, and the two fixation screws.
Figure 9:
FIG. 9 shows the two compression springs which are required to hold the jaws of both graspers in a closed position all the time.
Figure 10:
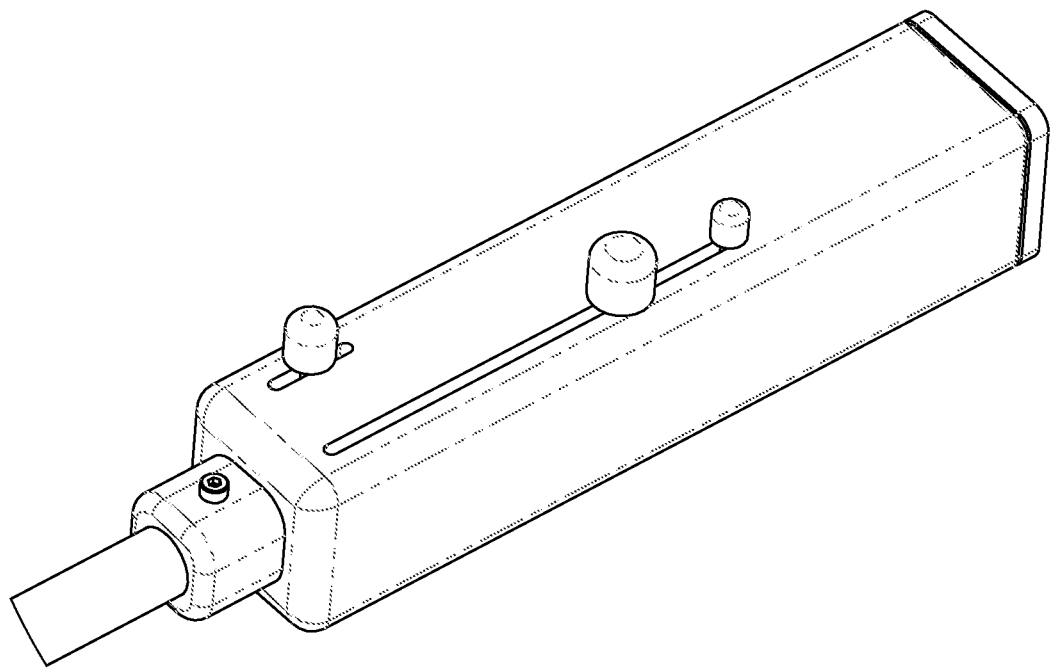
FIG. 10 is a perspective view of the handle showing the three operating push knobs on its upper surface.
Figure 11:
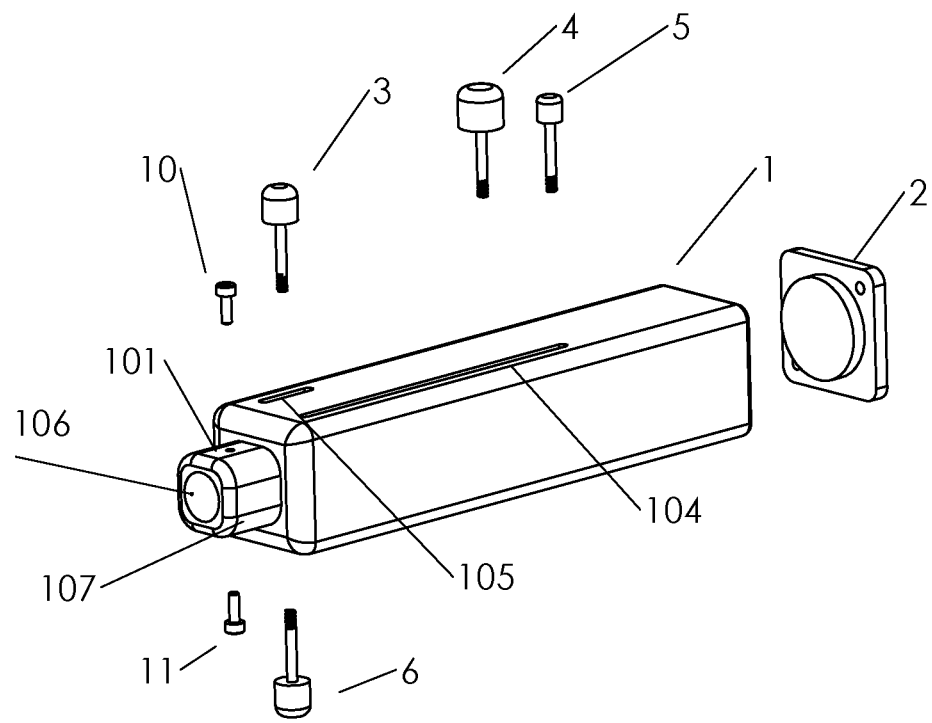
FIG. 11 is an exploded view of the parts in the handle subassembly. 1 refers to the handle itself, with a large round hollow cavity, open at its rear end, and extending to the neck in front. 2 is the rear end cap. 7 and 8 are the hexagonal screws which lock the main shaft to the neck of the handle. Knobs 3 and 6 are connected to the stationary grasper on the right side of the handle. Knob 3 on the upper side of the handle is pushed forwards by the thumb, thus opening up the jaws of the stationary grasper. Releasing it allows the jaws to close, holding the suture. The compression spring maintains the hold. Knob 6 on the underside of the handle may be further pulled back by the index finger, thus maintaining pressure on the jaws, which may be necessary to prevent the suture slipping out when the instrument is to pulled away from the knot to cinch it. 101 and 102 are female threads on the neck of the handle accepting the locking hexagonal screws 7 and 8. 103 is the lumen of the neck of the handle through which the main shaft passes. 104 is a long narrow slot on the left side of the upper surface of the handle, in which the pushing knob 4 slides forwards and backwards, extending or retracting the extendable grasper. The smaller knob 5 travels together with the entire extendable grasper, in this same slot 104, and is for controlling the jaws of the extendable grasper. 105 is a short slot on the right side of the upper surface of the handle near the front end, but is also through onto the bottom side, and is for knob 3 on the top and knob 6 on the bottom, which activate the jaws of the stationary grasper.
Figure 12:
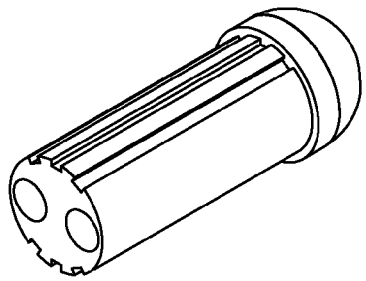
FIG. 12 is a perspective view of the front spacer 9, which is inserted into the front end of the main sheath 13. It bears a rounded outer tip, with 2 parallel small diameter lumens 108 and 109, through which the sheath of the graspers pass. Its upper and lower surfaces bear grooves 106, which provide extra room for retaining the adhesive.
Figure 12:
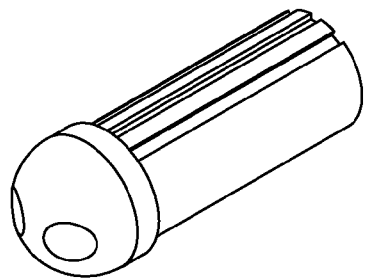
Figure 13:
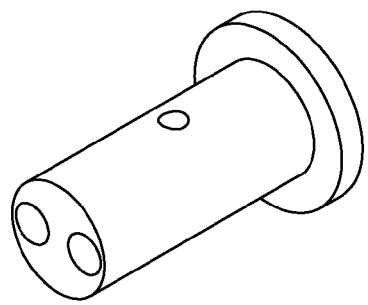
FIG. 13 is a perspective of the rear spacer, also with the same lumens 108 and 109, but with a wider flange, and female threads 107 for the locking hexagonal screws.
Figure 13:
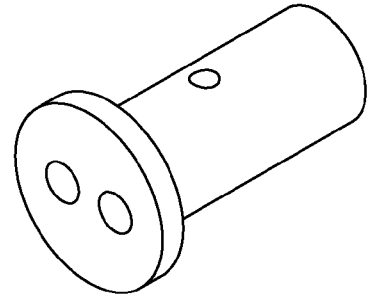
Figure 14:
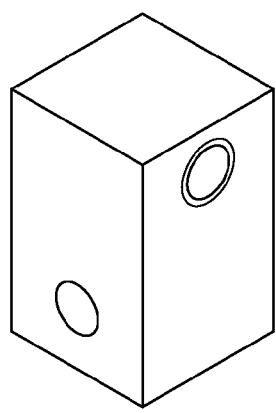
FIG. 14 is a perspective of the smaller connector 11, showing female thread 111 to receive the end of the operating rod of the graspers, and female thread 110 to receive the screw end of the knobs 3, 5, and 6, which are identical.
Figure 15:
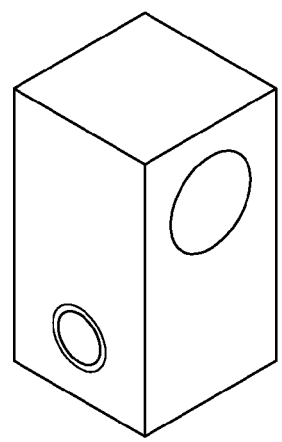
FIG. 15 is a perspective view of the slightly larger connector 12, showing a female thread for the operating rod 111, and a larger female hole to receive the sheath of the extendable grasper.
Figure 16:
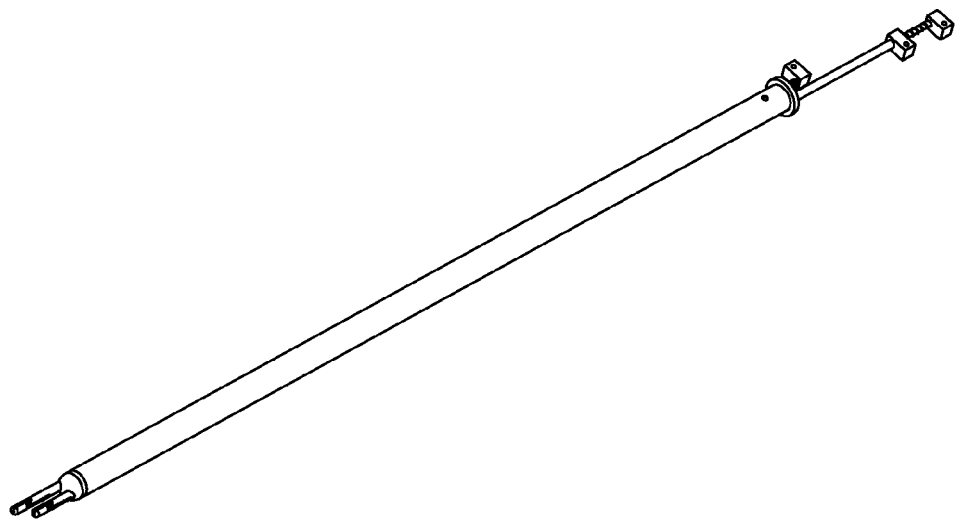
FIG. 16 is a perspective view of the entire main sheath sub-assembly, ready to be inserted into the rear end of the handle.
Figure 17:
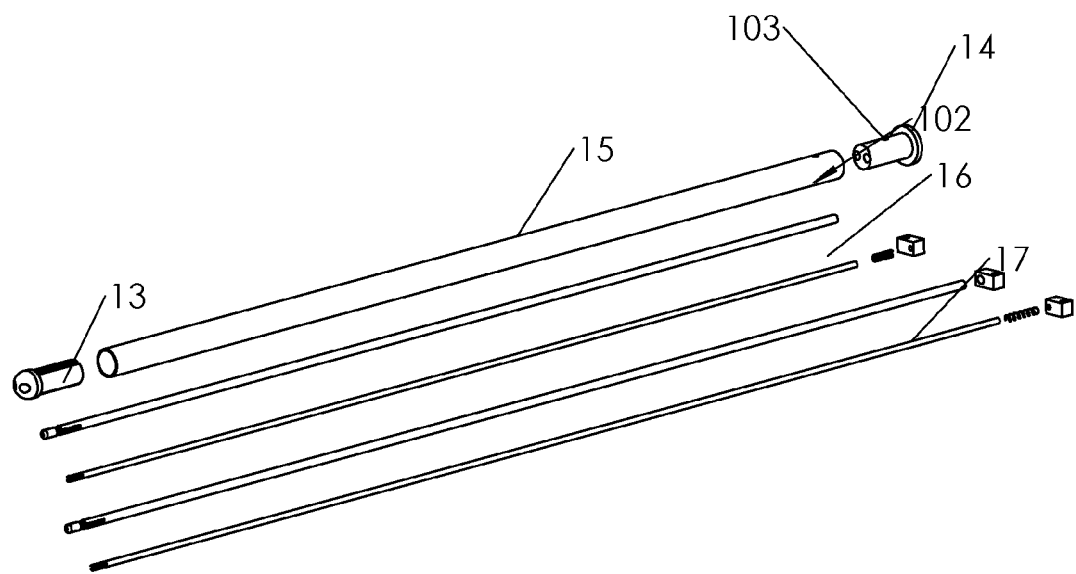
FIG. 17 is an exploded view of the components of this main sheath sub-assembly. Part 9 is the front spacer. Part 10 is the rear spacer. Part 11 is a smaller connector, of which there are 2, one for the rod of the stationary grasper, and the second for the rod of the extendable grasper. Part 12 is a slightly larger connector for the sheath of the extendable grasper. Part 13 is the main sheath. Part 14 is the sheath of the stationary grasper, and Part 15 is the rod of the stationary grasper. Part 16 is the sheath of the extendable grasper, and part 17 is the rod of the extendable grasper. Note parts 16 and 17 are intentionally longer than parts 14 and 15. Parts 18 and 19 are compression springs which are located over the proximal portions of the rods.
Figure 18:
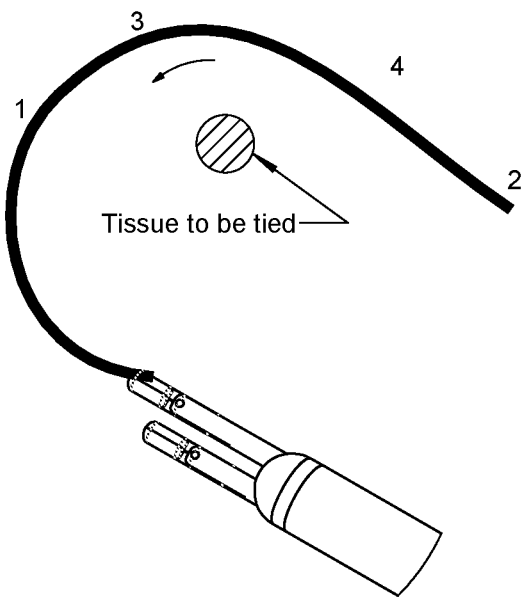
FIG. 18 is diagram showing the beginning of the knot tying process using the present invention, with the head end of the suture being grasped by the jaws of the stationary grasper.
Figure 19:
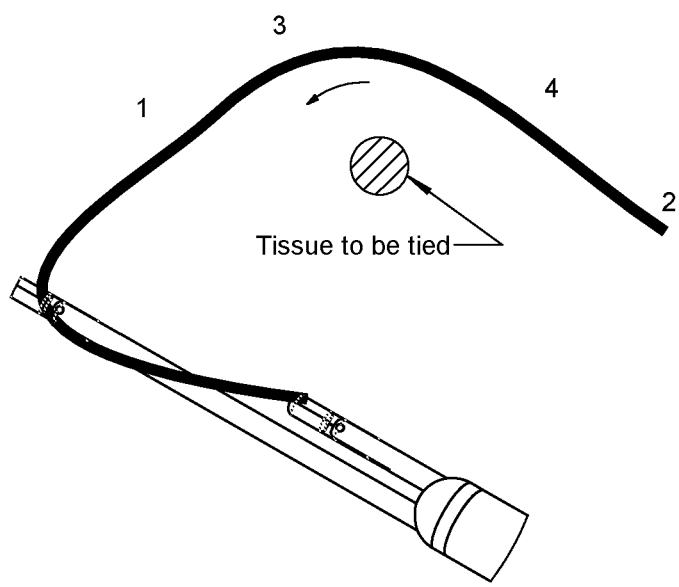
FIG. 19 shows the extendable grasper being fully extended out, and grasping the same suture a short distance further out.
Figure 20:
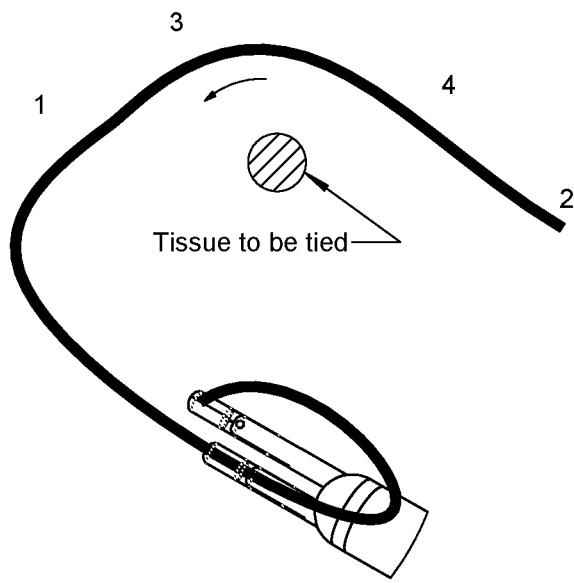
FIG. 20 shows the extendable grasper with the suture in its jaws, now retracted back to its starting position, which importantly is behind the tip of the stationary grasper.
Figure 21:
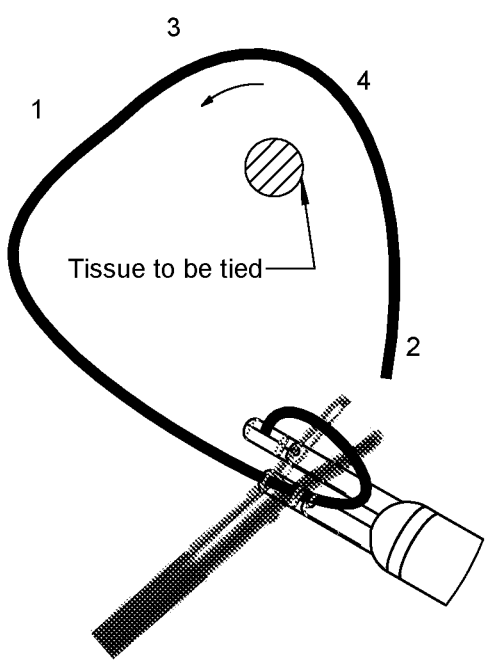
FIG. 21 shows a second instrument, a regular grasper held in the surgeon's other hand, now going through the loop, and pulling the tail end of the suture back through the loop, producing a tie.

The invention here deploys the following steps in tying a laparoscopic knot: First, the head end of the strand is grasped by the jaws of the stationary grasper, as shown in FIG. 18. Second, the extendable grasper is maximally extended out, as shown in FIG. 19. Third, the jaws of the extendable grasper are opened to grasp the same suture a short distance out. These jaws are then held closed by the action of the compression spring. Fourth, the extendable grasper is then pulled back to its original resting position, which is behind the jaws of the stationary grasper, creating a full crossing loop in the suture. Fifth, the tail end of the suture is then pulled through the loop, creating a tie. Finally, the jaws of the stationary grasper are further more tightly closed by pulling on the bottom trigger with the index finger, whilst the instrument is being pulled away from the knot to tighten it. The suture will be automatically pulled off the jaws of the retracted mobile grasper.

This instrument is generally held in the surgeon's dominant hand, whilst a regular grasper is held in the surgeon's other hand, which is used to pull the tail end of the suture through the loop, forming a knot. To be effective, the loop formed must be of the "closed" type, with the loop facing towards the tail end of the suture, and not away from it which would be the "open" type. Of note in the design is the uneven resting position of the tips of the two graspers, which is intended to create a crossing between the limbs of the suture forming the loop.

The invention claimed is:

1. A laparoscopic instrument for making a loop in a suture for intra-corporeal knot tying, comprising:
   two separate handleless graspers including a stationary grasper and an extendable grasper, said graspers being housed inside a common sheath forming a subassembly which is joined to a common in-line handle having control knobs located on a surface thereof;
   wherein said stationary grasper is configured to remain stationary relative to said sheath and has a first length measured from a distal end to a proximal end thereof;
   wherein said extendable grasper is configured to be extendable and retractable relative to said sheath and has a second length measured from a distal end to a proximal end thereof, said second length being greater than said first length;
   wherein said graspers and jaws of said graspers are configured to be activated by a user's thumb pushing or pulling on the control knobs in conjunction with compression springs located within said handle; and
   wherein slots on the surface of said handle permit the control knobs to open the jaws of said graspers and further permit extension and retraction of said extendable grasper.

2. A method of creating a loop in a suture for tying a suture knot using the laparoscopic instrument of claim 1, the method comprising:
   simultaneously grasping a suture at two points a sufficient distance apart with said graspers, bringing the two points of the suture together by retracting said extendable grasper using the control knobs of said handle, and producing a loop in the suture.

\* \* \* \* \*